US009643012B2

(12) United States Patent
Averina et al.

(10) Patent No.: US 9,643,012 B2
(45) Date of Patent: May 9, 2017

(54) ALGORITHM ADAPTATION TO AN EXTERNAL IMPACT ON THE DATA

(71) Applicant: Cardiac Pacemakers, Inc., St. Paul, MN (US)

(72) Inventors: Viktoria A. Averina, Roseville, MN (US); Pramodsingh Hirasingh Thakur, Woodbury, MN (US); Yi Zhang, Plymouth, MN (US); Qi An, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 99 days.

(21) Appl. No.: 14/178,078

(22) Filed: Feb. 11, 2014

(65) Prior Publication Data

US 2014/0236029 A1     Aug. 21, 2014

Related U.S. Application Data

(60) Provisional application No. 61/765,920, filed on Feb. 18, 2013.

(51) Int. Cl.
    *A61N 1/36*          (2006.01)
    *A61N 1/362*       (2006.01)
                   (Continued)

(52) U.S. Cl.
    CPC ........ *A61N 1/3627* (2013.01); *A61B 5/02055* (2013.01); *A61B 5/0452* (2013.01);
                  (Continued)

(58) Field of Classification Search
    CPC ....... A61B 5/7221; A61N 1/37; A61N 1/3702
    See application file for complete search history.

(56) References Cited

U.S. PATENT DOCUMENTS 7,761,158 B2    7/2010   Brockway et al.
7,996,082 B2    8/2011   Palreddy et al.
               (Continued)

FOREIGN PATENT DOCUMENTS

| CN | 105050656 | 11/2015 |
|---|---|---|
| WO | 2009111764 | 9/2009 |
| WO | 2014126934 | 8/2014 |

OTHER PUBLICATIONS

"International Preliminary Report on Patentability," for PCT/US2014/015853 mailed Aug. 27, 2015 (9 pages).

(Continued)

*Primary Examiner* — George Evansiko
(74) *Attorney, Agent, or Firm* — Pauly, DeVries Smith & Deffner, L.L.C.

(57) ABSTRACT

Devices and methods for detecting a physiological target event such as events indicative of HF decompensation status are described. An ambulatory medical device is configured to determine the presence and timing of a confounding event, segment a sensed physiological signal into at least two data segments, adjust the physiological signal by removing or lessening the impact of the confounding event on the physiological signal. The adjusted data can be presented to the user, and the ambulatory medical device can detect the target events using the adjusted physiologic signal. In some embodiments, the ambulatory medical device can be configured to detect an event indicative of HF decompensation using a physiological signal and the information of the detected confounding event.

9 Claims, 11 Drawing Sheets

(51) Int. Cl.
*A61B 5/0205* (2006.01)
*A61B 5/0452* (2006.01)
*A61B 5/00* (2006.01)

(52) U.S. Cl.
CPC ............ *A61B 5/7221* (2013.01); *A61B 5/686* (2013.01); *A61B 5/7278* (2013.01); *A61B 2560/0276* (2013.01)

(56) References Cited

U.S. PATENT DOCUMENTS

| | | |
|---|---|---|
| 8,200,341 B2 | 6/2012 | Sanghera et al. |
| 2005/0143779 A1 | 6/2005 | Libbus et al. |
| 2006/0247706 A1 | 11/2006 | Germanson et al. |
| 2008/0157980 A1 | 7/2008 | Sachanandani et al. |
| 2010/0223013 A1 | 9/2010 | Kamath et al. |
| 2010/0223022 A1 | 9/2010 | Kamath et al. |
| 2010/0228109 A1 | 9/2010 | Kamath et al. |
| 2011/0009760 A1 | 1/2011 | Zhang et al. |
| 2011/0098585 A1* | 4/2011 | Warren ............... A61B 5/0452 600/509 |
| 2011/0105929 A1 | 5/2011 | Sharma et al. |
| 2012/0157864 A1 | 6/2012 | Thakur et al. |

OTHER PUBLICATIONS

"International Search Report and Written Opinion," for PCT/US2014/015853, mailed Apr. 25, 2014 (12 pages).

"Communication Pursuant to Rules 161(1) and 162 EPC," for European Patent Application No. 14707047.8, mailed Sep. 30, 2015 (2 pages).

"Response to Communication Pursuant to Rules 161(1) and 162 EPC," for European Patent Application No. 14707047.8, filed with the EPO Mar. 22, 2016 (29 pages).

"First Office Action," for Chinese Patent Application No. 201480017229.4 mailed Jun. 2, 2016 (18 pages) with English Translation.

\* cited by examiner

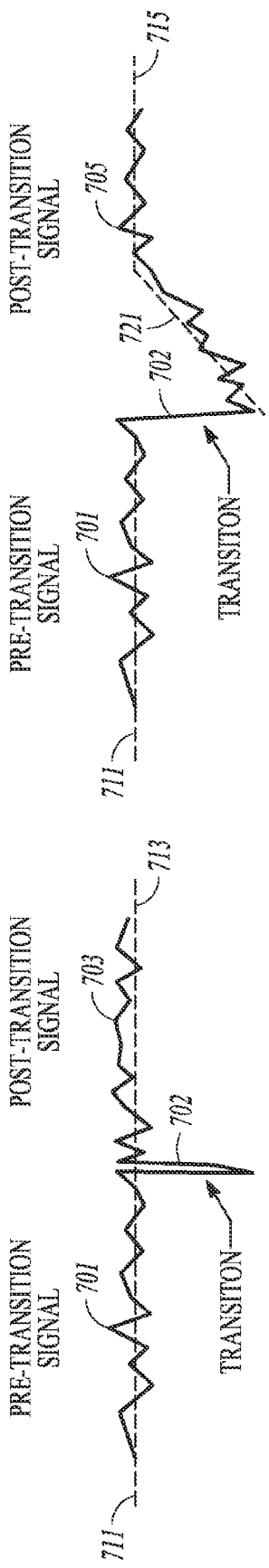
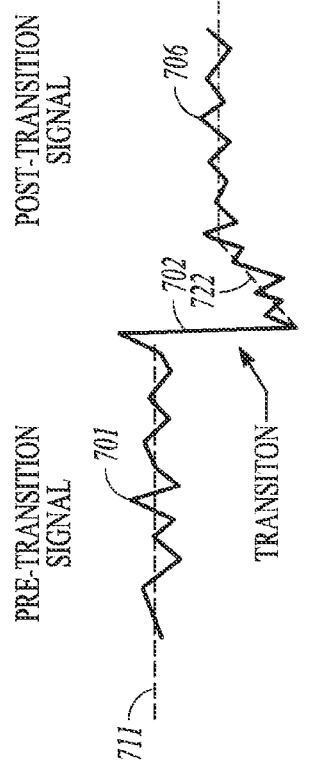
FIG. 7A
FIG. 7B
FIG. 7C
FIG. 7D

US 9,643,012 B2

ALGORITHM ADAPTATION TO AN EXTERNAL IMPACT ON THE DATA

CLAIM OF PRIORITY

This application claims the benefit of priority under 35 U.S.C. §119(e) of U.S. Provisional Patent Application Ser. No. 61/765,920, filed on Feb. 18, 2013, which is herein incorporated by reference in its entirety.

TECHNICAL FIELD

This document relates generally to medical devices, and more particularly, to systems, devices and methods for detecting a physiologic event or monitoring a physiologic condition of a patient.

BACKGROUND

Congestive heart failure (CHF) is a major health problem and affects over five million people in the United States alone. CHF patients typically have enlarged heart with weakened cardiac muscles, resulting in poor cardiac output of blood. Elevated pulmonary vascular pressures can cause fluid accumulation in the lungs over time. In many CHF patients, fluid accumulation precedes episodes of heart failure (HF) decompensation.

SUMMARY

Frequent monitoring of CHF patients and timely detection of intrathoracic fluid accumulation or other events indicative of HF decompensation status can help prevent worsening of HF in CHF patients, hence reducing cost associated with HF hospitalization.

Ambulatory medical devices can be used for monitoring HF patient and detecting HF decompensation events. Examples of such ambulatory medical devices can include implantable medical devices (IMD), subcutaneous medical devices, wearable medical devices or other external medical devices. The ambulatory or implantable medical devices can be configured to sense electrical activity and mechanical function of the heart, and to optionally deliver therapy such as electrical stimulation pulses to a target area, such as to restore or improve the cardiac function.

Some of these devices can include one or more diagnostic features, such as using a physiological signal to detect a physiologic event or monitoring a physiologic condition. The physiological signal may be affected by confounding events which can be different than a target physiological event or condition of interest. The confounding event may be physiological or non-physiological in nature. For example, in monitoring an HF patient or in detecting a HF decompensation event such as in an IMD using a physiological signal, events such as lead revision, change of pacing configuration, or a replacement of the device either at the same location or at a different location may leave a signature on the physiological signal, thereby being erroneously interpreted by the user or erroneously detected by the IMD as a target HF decompensation event. One type of erroneous detection is false positive detection, where a confounding event is mis-detected as a target HF decompensation event. A false positive detection may cause unnecessary intervention and additional healthcare cost. Another type of erroneous detection is false negative detection, where a true target HF decompensation event is mis-detected as a non-target event. A false negative detection may delay or miss a necessary intervention or therapy. Therefore, the present inventors have recognized that there remains a considerable need of devices and methods that can detect target physiological events with reduced false negative and false positive detections, particularly in the presence of confounding events.

Various embodiments described herein can help improve the process of detecting physiological events of interest or monitoring a patient's condition. For example, an ambulatory medical device (such as an implantable medical device or a wearable medical device) can detect a target physiologic event such as using confounding event information. A signal receiver circuit can be configured to receive a physiologic signal. A confounding event detector circuit can be configured to receive a confounding event bearing (CEB) signal and determine the presence of a confounding event from the CEB signal. A signal processing circuit can be configured to adjust the physiological signal using the detected confounding event. A physiologic target event or condition detector circuit can be configured to detect a target event from the adjusted physiologic signal.

A method can include detecting a target physiologic event in a patient having an ambulatory medical device. The method can include receiving a physiologic signal, detecting a confounding event from one or more CEB signal, segmenting the physiological signal into at least two data segments using the characteristics of the detected confounding event, adjusting one or more data segment to remove or lessen the impact of the confounding event on the physiological signal, and detecting a physiologic target event by applying a target event detection algorithm to the adjusted physiological signal.

A method for detecting an event indicative of HF decompensation status can include sensing an impedance signal from a patient, detecting a confounding event using whether a rate of change of the impedance signal intensity is within a specified physiologic range, segmenting the impedance signal into two data segments using a characteristic parameter of the detected confounding event, the characteristic parameter including a start time of the detected confounding event, adjusting the impedance signal by subtracting from one segment a difference between the average intensities between the two segments, or applying a HF decompensation detection algorithm to the adjusted impedance signal to detect the target event indicative of HF decompensation status.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 7A-D illustrate examples of impacts of confounding events on confounding event bearing (CEB) physiological signals.

DETAILED DESCRIPTION

Disclosed herein are systems, devices and methods for detecting physiologic target events using the information of one or more confounding events. The physiologic target events can include early precursors of an HF decompensation episode. That is, these events can occur well before the systematic manifestation of worsening of HF. Therefore, by detecting the precursor events, the present document can provide a method and device to predict the impending HF decompensation episode in the presence of one or more confounding events. The methods and devices described herein can also be applicable to predicting the progression or worsening of a disease or a patient's health condition, to stratifying a patient's risk of developing a disease or a condition, or to monitoring a patient's health status or response to a medical intervention and to providing feedback to the healthcare professionals engaged in patient management.

Figure 1:
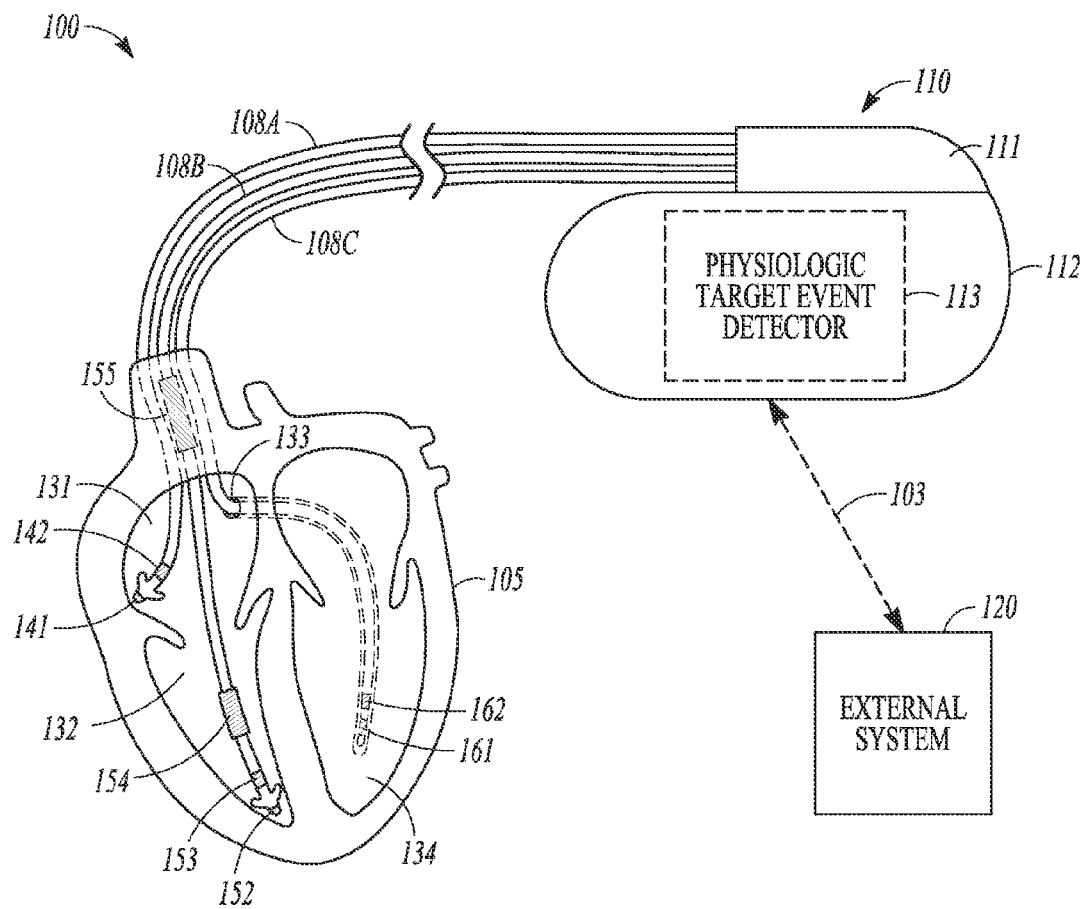
FIG. 1 illustrates an example of cardiac rhythm management (CRM) system and portions of the environment in which the CRM system operates.

FIG. 1 illustrates an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). The IMD 110 can include one or more monitoring or therapeutic devices such as a subcutaneously implanted device, a wearable external device, a neural stimulator, a drug delivery device, a biological therapy device, or one or more other ambulatory medical devices. The IMD 110 may be coupled to, or may be substituted by a monitoring medical device such as a bedside or other external monitor.

As illustrated in FIG. 1, the IMD 110 can include a hermetically sealed can 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing of the LV electrogram and optionally allow delivery of one or more resynchronization pacing pulses from the LV.

The IMD 110 can include an electronic circuit that can sense a physiological signal. The physiological signal can include an electrogram or a signal representing mechanical function of the heart 105. The hermetically sealed can 112 may function as an electrode such as for sensing or pulse delivery. For example, an electrode from one or more of the leads 108A-C may be used together with the can 112 such as for unipolar sensing of an electrogram or for delivering one or more pacing pulses. A defibrillation electrode from the lead 108B may be used together with the can 112 such as for delivering one or more cardioversion/defibrillation pulses. In an example, the IMD 110 can sense impedance such as between electrodes located on one or more of the leads 108A-C or the can 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiological sensors that can be integrated within the IMD 110. The IMD 110 can also be configured to sense a physiological signal from one or more external physiologic sensors or one or more external electrodes that can be coupled to the IMD 110. Examples of the physiological signal can include one or more of intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are.

As illustrated, the CRM system 100 can include a physiologic target event detector 113. The physiologic target event detector 113 can include a confounding event detector that can detect and characterize a confounding event in a physiological signal, a signal processing unit that processes the physiological signal, and a target event detector to detect the target event from the processed physiological signal. The confounding event detector can detect the physiologic state using a first signal acquired from the electrodes on the leads 108A-C, and the target event detector can detect the target event using a second signal acquired from the electrodes on one or more of the leads 108A-C. The first signal used by the confounding event detector and the second signal used for target event detection can be obtained from the same physiological signal. Examples of physiologic target event detector 113 are discussed below, such as with reference to FIGS. 2-5.

The external system 120 can allow for programming of the IMD 110 and can receives information about one or more signals acquired by IMD 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that can include physiological data acquisition such as using programmably specifiable sensing electrodes and configuration, device self-diagnostic test, or delivery of one or more therapies.

The physiologic target event detector 113 may be implemented at the external system 120, which can be configured to perform target event detection such as using data extracted from the IMD 110 or data stored in a memory within the external system 120. Portions of the physiologic target event detector 113 may be distributed between the IMD 110 and the external system 120.

Portions of the IMD 110 or the external system 120 can be implemented using hardware, software, or any combination of hardware and software. Portions of the IMD 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals.

Figure 2:
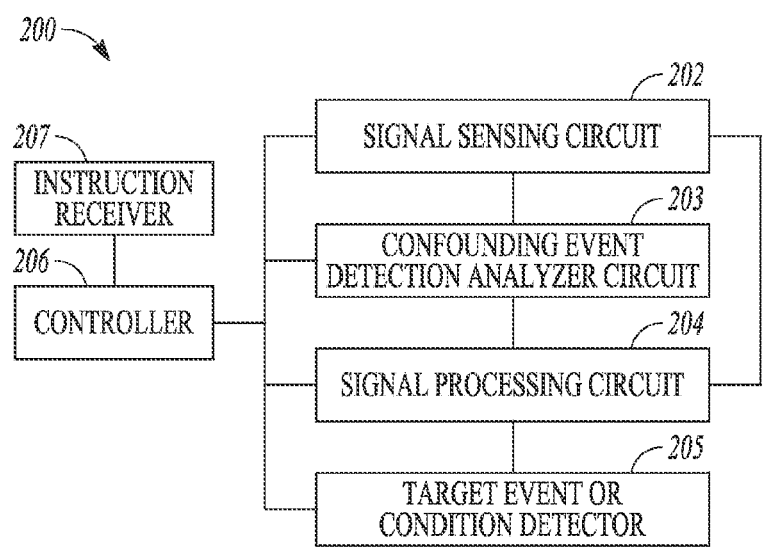
FIG. 2 illustrates an example of a physiologic target event detector.

FIG. 2 illustrates an example of a target event detector 200, which can be an embodiment of physiologic target event detector 113. The target event detector 200 can include a signal receiver circuit 202, a confounding event detection and analysis circuit 203, a signal processing circuit 204, a target event or condition detector 205, a controller 206, and an instruction receiver 207.

The signal receiver circuit 202 can receive one or more signals indicative of a patient's physiologic state. Examples of the physiological signal can include electrograms from electrodes on leads 108A-C and the can 112, intrathoracic impedance, intracardiac impedance, arterial pressure, pulmonary artery pressure, RV pressure, LV coronary pressure, coronary blood temperature, blood oxygen saturation, heart sounds, or respiration signals including respiration rate or tidal volume. In an example, the signal receiver circuit can be configured to couple to a signal sensing circuit which senses the physiologic signal. The signal sensing circuit can be coupled to the electrodes such as on one or more of the leads 108A-C and IMD can 112 connected to an ambulatory medical device. Alternatively, the signal sensing circuit can be coupled to electrodes on one or more of implantable subcutaneous leads, or to external physiologic sensors. In an example, the signal receiver circuit can be coupled to a memory circuit and receive the physiological data stored in the memory circuit.

The confounding event detection and analysis circuit 203 can detect a confounding event from a confounding event-bearing (CEB) signal or other sources containing information about the confounding event, and characterize the detected confounding event. A confounding event can be an event other than the physiologic target event or condition but could be mis-detected or mis-classified by a target event detector as a physiologic target event. For example, in detecting a target event indicative of HF decompensation, a confounding event can be non-physiologic in nature and include, for example, device reprogramming, revision of an ambulatory medical device or leads and other components associated with the device, surgical interventions, posture changes, electromagnetic interference, or other changes in the device and environment that affect the CEB signal but are not generally indicative of the patient's physiologic state of interest. The CEB signal used for detecting a confounding event can be a physiological signal different than the received signal from the signal receiver circuit 202 used for detecting a target event. The CEB signal can be the same signal as the received signal from the signal receiver circuit 202.

The signal processing circuit 204 can receive input from the signal receiver circuit 202 and the confounding event detection and analysis circuit 203, and perform signal processing on the received signal 202. In an example, the signal processing circuit 204 can include circuits for segmenting the received signal and adjusting the segmented signal.

The target event or condition detector 205 can detect a pre-determined target event or condition such as using the processed signal from signal processing circuit 204. A target event can include an event or condition indicative of an onset of a disease, worsening of a disease state, or a change of a disease state. Examples of target event can include a worsening HF, HF decompensation, pulmonary edema, or myocardial infarction.

The controller 206 can control the operations of functional blocks 202 through 205 and the data flow between these functional blocks. The controller 206 can receive external programming input from the instruction receiver 207 to control the signal sensing, physiological state analysis, and HF decompensation event detection. Examples of the instructions received by instruction receiver 206 may include: selection of electrodes used for sensing physiological signals, selection of source of data used for confounding event detection, selection of confounding event detection algorithms and the associated parameter, or configuration of the target event and condition detector 205. In an example, the instruction receiver 207 is coupled to a user interface on the external system 120. The external system 120 can be configured to present programming options to the user and receive user's programming input.

Figure 3:
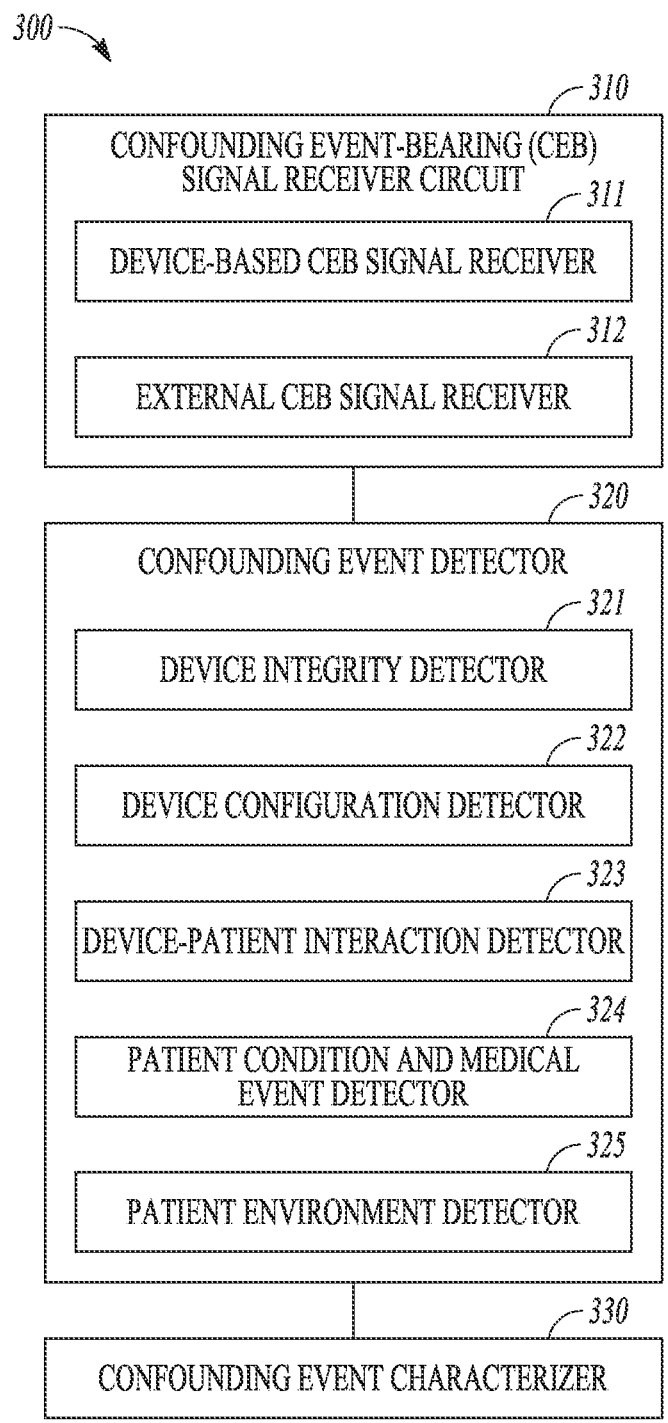
FIG. 3 illustrates an example of a confounding event detection and analysis circuit.

FIG. 3 illustrates an example of confounding event detection and analysis circuit 300, which can be an embodiment of confounding event detection and analysis circuit 203. The confounding event detection and analysis circuit 300 can include a CEB signal receiver circuit 310, a confounding event detector 320, and a confounding event characterizer 330.

The CEB signal receiver circuit 310 can receive a CEB signal from a device-based CEB signal receiver 311 or an external CEB signal receiver 312. The device-based CEB signal receiver 311 can receive signals from an ambulatory medical device such as the IMD 110, a physiologic monitor, or a memory where the physiologic data are stored. In an example, the CEB signal and the physiological signal acquired by the signal receiver circuit 202 and used for detecting target event or condition can be obtained from the same physiological signal. In another example, the CEB signal can be acquired from the signal receiver circuit 202 but undergo different signal processing than the signal for detecting target event. For example, the CEB signal can be a respiration rate signal derived from an impedance signal sensed by a transthoracic impedance sensing circuit, while the physiological signal used for target event detection can be a total impedance signal obtained from the same transthoracic impedance sensing circuit. In another example, the CEB signal and the physiological signal received by the signal receiver circuit 202 can be from different ambulatory sensors or electrodes connected to the ambulatory medical devices. For example, the CEB signal can be a heart sound signal obtained from an accelerometer sensor, while the physiological signal received by the signal receiver circuit 202 can be from an impedance sensing circuit.

In some examples, the CEB signal can include non-physiologic data that are indicative of device condition and function, such as frequent lead impedance measurement that provides information about device integrity. A confounding event can leave a signature not only in a physiological signal, but also in non-physiological signals such as signals representing device condition and function. For example, a confounding event of electromagnetic interference (EMI) may cause morphological changes in intracardiac electrograms as well as in lead impedance signals used for monitoring device condition and functionality. In an example, the CEB signal receiver circuit 310 can automatically select one or more physiological or non-physiological CEB signals using the information of the type of confounding event it sets to detect.

The external CEB signal receiver 312 can receive signal from sources external to ambulatory medical devices or monitors. In an example, the external CEB signals can include a clinical report, a medical record, a lab test report, or a case report form. In another example, the external CEB signals can include signals from another ambulatory medical device. The clinical report may have textual or graphical information about the confounding event. In another example, the external CEB signal receiver 312 can receive environmental sensor signals, such as environmental temperature, humidity, atmospheric pressure, or other measurements of the patient's environment.

Figure 9:
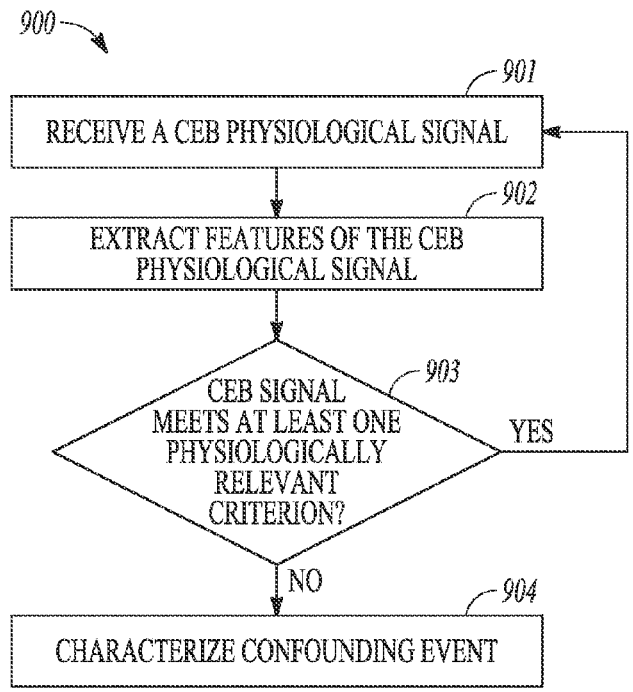
FIG. 9 illustrates an example of a method for detecting and characterizing a confounding event such as using physiologically relevant data range.

The confounding event detector 320 can receive the input from the CEB signal receiver circuit 310 and detects a confounding event from one or more of CEB physiological signals, CEB signals representing device functionality, CEB clinical reports, or CEB environmental data. The confounding event detector 320 can include a plurality of detectors to account for various types of confounding events. Specifically, the confounding event detector 320 can include one or more of a device integrity detector 321, a device configuration detector 322, a device-patient interaction detector 323, a patient condition and medical event detector 324, or a patient environment detector 325. Examples of method used by the confounding event detector are discussed below, such as with reference to FIGS. 9-11.

The device integrity detector 321 can detect an event indicative of the integrity of an ambulatory medical device and associated electrodes, leads, and sensors. Examples of the confounding events indicative of the device integrity can include a change of mechanical or electrical property of components within the ambulatory medical device, leads, or sensors and a change of mechanical or electrical coupling among the ambulatory medical device, the leads, or the sensors, such as dislodgement or loose connection.

The device configuration detector 322 can detect the change of configuration of the ambulatory device. Examples of the confounding events associated with the device configuration change can include a change of device programming that affects device operation (e.g., sensing and therapy delivery) including changes in one or more of pacing mode, pacing vector, pacing pulse parameters, pacing control parameters, electrogram sensing vector, or mechanical or physiological signals sensing vector.

The device-patient interaction detector 323 can detect a change of the interaction between the patient and one or more of the ambulatory medical device, the leads, or the sensors associated with the device. Examples of the confounding events associated with the device-patient interaction can include lead revision or replacement, lead dislodgement, device pocket revision, pocket infection, new device placement, or a replacement of a device.

The patient condition and medical event detector 324 can detect an event or condition associated with the patient's health condition or medical status other than the physiologic target event. For example, in the context of detecting a target event indicative of HF decompensation, confounding events associated with the patient condition and medical event can include onset of myocardial infarction, cardiac arrest, pulmonary diseases, a change of patient's medication, a change of the patient's activity level, a change of posture, a surgical intervention, or a change of patient's psychological state.

The patient environment detector 325 can detect a change in patient environment, including a change in temperature, humidity, atmospheric pressure, time and seasonal change, or indication of patient's exposure to electromagnetic interferences.

The confounding event characterizer 330 can compute characteristic parameters of the detected confounding events. In an example, the characteristic parameters can include a start time, a stop time, a duration, a type, or other contextual information about the detected confounding event.

Figure 4:
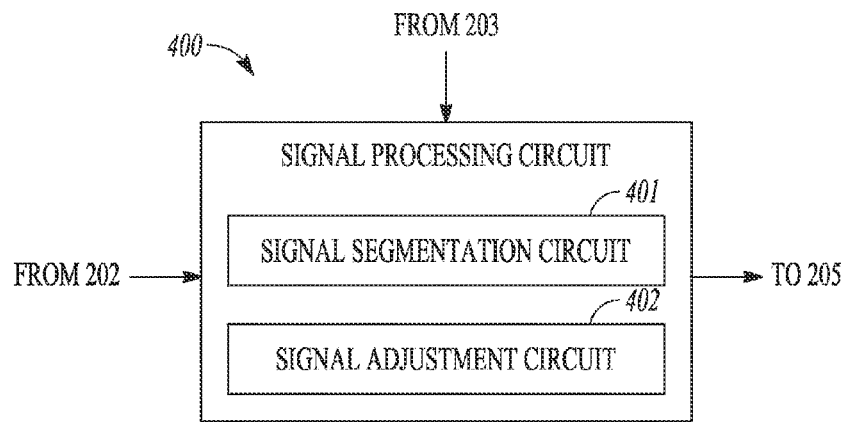
FIG. 4 illustrates an example of a signal processing circuit.

FIG. 4 illustrates an example of a signal processing circuit 400, which can be an embodiment of signal processing circuit 204. The signal processing circuit 400 can include a signal segmentation circuit 401 and a signal adjustment circuit 402. The signal processing circuit 400 can receive the physiological signal from the signal receiver circuit 202 and the confounding event characteristics from the confounding event detection and analysis circuit 203, and adjust the physiological signal such as using the confounding event characteristics.

The signal segmentation circuit 401 can segment the physiological signal into at least two segments such as using the characteristics of the confounding event. In an example, the start time of the confounding event creates a transition in the physiological signal, and the two segments of the physiological signals are identified as a pre-transition segment (i.e., data before the start time of the confounding event) and a post-transition segment (i.e., data after the start time of the confounding event).

The signal adjustment circuit 402 can adjust the physiologic signal to remove or lessen the impact of the confounding event on the physiological signal. The adjustment can be performed on the pre-transition signal, the post-transition signal, or both. The adjustment of a first segment of the signal (e.g., the post-transition signal) can be made relative to signal characteristics of a second segment of the signal (e.g., the pre-transition signal). In an example, the adjustment of a segment of the signal can be made without reference to other segment(s) of the signal. The signal adjustment circuit 402 can be configured to be capable of adjusting one segment independently of the adjustment of other segment(s). Examples of signal segmentation and adjustment such as using the information of the detected confounding event are discussed below, such as with reference to FIGS. 12-14.

Figure 5:
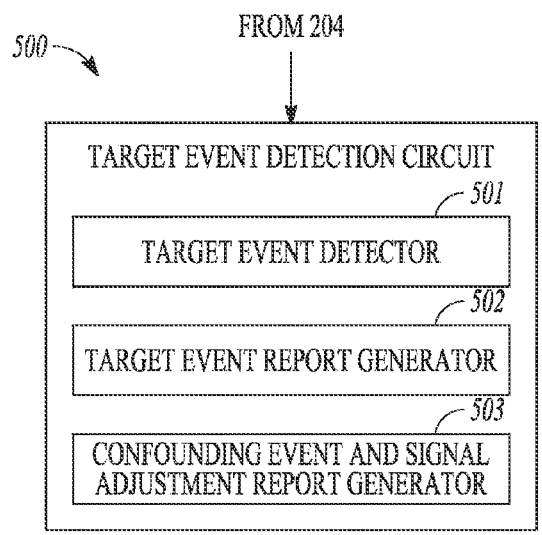
FIG. 5 illustrates an example of a physiologic target event detection circuit.

FIG. 5 illustrates an example of target event detection circuit 500, which can be an embodiment of target event detection circuit 205. The target event detection circuit 500 can include a target event detector 501, a target event report generator 502, and a confounding event and signal adjustment report generator 503. The target event detection circuit 500 can receive the adjusted physiological signal from the signal processing circuit 204 and detects the target event from the adjusted physiologic signal.

The target event detector 501 can detect the target event from the adjusted physiological signal. In an example, the target event can be an event indicative of HF decompensation status, and the target event detector 501 can be configured to compute an HF decompensation index such as using the adjusted physiological data and determine whether an event indicative of HF decompensation is detected such as by comparing the HF decompensation index to a threshold value. Examples of target HF decompensation event detection using the confounding event information are discussed below, such as with reference to FIGS. 12 and 15.

The target event report generator 502 can generate a report to inform the user the detected target event. Examples of the report can include a textual or graphical message, a sound, an image, or a combination thereof. In an example, the target event report generator 502 can be coupled to the external device 120 and the report can be presented to the user via the external device 120.

The confounding event and signal adjustment report generator 503 cam generate a report and present to the user information including detected confounding event, the adjustment of the physiological signal, or both. In an example, the confounding event and signal adjustment report generator 503 can be coupled to the external device 120, and the report can be presented to the user via the external device 120. In another example, the presentation of the report and the user input can be performed interactively on the external device 120. For example, the external device 120 can be configured to receive input from the user, and the confounding event, and the signal adjustment report generator 503 can be configured to receive the user input from the external device 120. The user input can include confirmation, storage, or other programming instructions to operate on the detected confounding events or the adjusted physiological signal.

Figure 6:
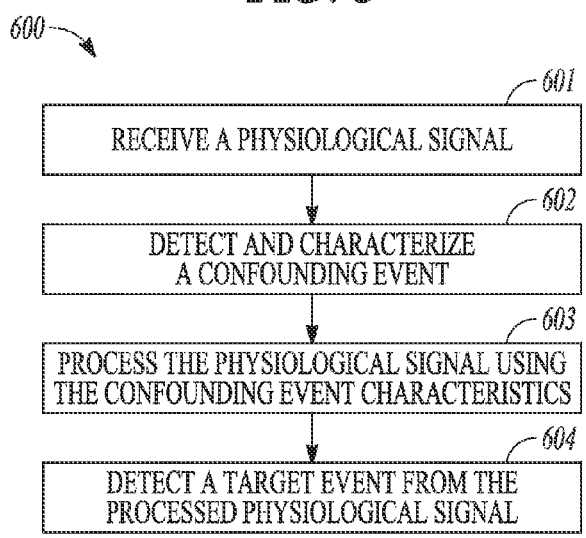
FIG. 6 illustrates an example of a method for detecting a physiologic target event adapted to characteristics of a confounding event.

FIG. 6 illustrates an example of a method 600 for detecting a target event from a physiological signal. The method 600 can be implemented and operate in an ambulatory medical device or in a remote patient management system. In an example, the method 600 can be performed by physiologic target event detection circuit 113 implemented in IMD 110, or the external device 120 which can be in communication with the IMD 110.

At 601, a physiological signal can be received. The physiological signal may represent electrical or mechanical activities in the body. Examples of the physiological signal include: heart rate, heart rate variation, conduction times, arrhythmias, intrathoracic impedance, intracardiac impedance, arterial pressure, pulmonary artery pressure, RV pressure, LV coronary pressure, heart sounds, respiration signals including respiration rate or tidal volume; coronary blood temperature, blood oxygen saturation, electrolyte concentrations, or other measures descriptive of the patient's physiology. The physiological signal can be received from a signal sensing circuit coupled to the electrodes on one or more of the leads such as 108A-C, or external sensors associated with an ambulatory medical device. The physiologic signal can also be received from a signal memory where the physiological data are stored.

At 602, a confounding event can be detected from a CEB signal. One type of confounding event can be associated with the patient's health condition or medical status other than the physiologic target event, such as events indicative of myocardial infarction, an event of cardiac arrest, a change of patient's medication, a change of activity level, a change of posture, a surgical intervention, or a change in psychological state. Another type of confounding event can be related to changes in device configuration, device integrity, device-patient interactions, or patient's environment. Examples of confounding events associated with the device integrity can include a change of mechanical or electrical property of components within the ambulatory medical device, the lead, or sensors; a change of mechanical or electrical coupling among the ambulatory medical device, the lead, or sensors, including a dislodgement and a loose connection. Examples of confounding events associated with the device configuration change can also include a change of device programming that affects the mode of operation, such as changes in pacing mode, pacing vector, pacing parameters and pacing control parameters, electrical signal sensing vector, or mechanical or physiological signals sensing vector. Examples of confounding events associated with the device-patient interaction can include an implantable lead revision, a device pocket revision, a new device implant, or a replacement of a device either at the same or at a different location. Examples of confounding events associated with the patient environment can include a change in temperature, humidity, atmospheric pressure, time and seasonal change, or indication of patient's exposure to electromagnetic interferences.

The CEB signals can include signals from ambulatory devices, monitors, or sensors. Examples of device data can include the patient's physiologic signals, or signals indicative of the device condition and function. In an example, the CEB signal and the physiological signal acquired by signal receiver circuit 202 used for target event detection can be obtained from the same physiological signal. In another example, the CEB signal can be acquired from the same signal receiver circuit 202 but undergo different filtering or other signal processing than the signal used for target event detection. In another example, the CEB signal and the physiologic signal obtained from the signal receiver circuit 202 can be obtained from different ambulatory sensors or electrodes coupled to the ambulatory medical devices.

The CEB signals can also include data from sources external to devices or sensors. Examples of signals from external sources can include a clinical report, a medical record, a lab test report, a case report form, a physician's input on a device programmer, or a signal from another ambulatory medical device. The external CEB signals can include environmental sensor signals such as environmental temperature, humidity, atmospheric pressure, or other measurements of the patient's environment.

Once a confounding event is detected, a number of parameters that characterize the detected confounding event can be computed at 602. Examples of the characteristic parameters can include a start time, a stop time, a duration, a type, or contextual information about the detected confounding event.

At 603, the received physiological signal can be processed to remove or lessen the impact of the confounding event on the physiological signal. In an example, the method of signal processing can be performed by signal processing circuit 400, where the physiological signal can be segmented and adjusted such as using the characteristics of the detected confounding events. At 604, the processed physiological signal can be used to detect a target event. In an example, the method of target event detection can be performed by the target event detection circuit 500. Examples of the methods for physiological signal adjustment and target event detection using the information of the confounding event are discussed below, such as with reference to FIGS. 12-15.

FIGS. 7A-D illustrate examples of impacts of confounding events on CEB physiological signals. The CEB signal can include a physiological signal, a signal representing the device condition or functionality, or a signal representing a medical event or change in patient condition, such as a surgery. In an example, the signals illustrated on FIGS. 7A-D can be received from the device-based CEB signal receiver circuit 311.

A confounding event on a CEB signal may be characterized by morphological changes on the CEB signal, including morphologies during signal transition and during signal recovery. For example, while slow and gradual transitions may typically be a result of an underlying physiologic change in the patient, sharp and transient transitions in the signal are more likely due to a non-physiologic confounding event. The transiency of a transition can be determined using the information of the time scale of target event of interest. For example, the transition can be considered transient if it is within 1-5 hours, within 1-2 days, or within 1-2 weeks.

Several patterns of transitional morphologies and recovery morphologies have been identified. For example, signal transition may be transient or gradual, and signal recovery may be a full recovery (i.e., recovery to the pre-trigger signal intensity level) or a reset recovery (i.e., recovery to a steady-state level different than the pre-trigger signal level). FIG. 7A illustrates an example of a confounding event with transient transition with full recovery. This may be identified as "spike noise" on the CEB signal, where the confounding event signature 702 lasts for a very short period of time. Following the transition, the post-transition signal 703 has an average intensity 713 comparable to the average signal intensity 711 of the pre-transition signal 701. FIG. 7B illustrates an example of a confounding event with transient transition with reset recovery. Following a brief transition 702, the post-transition signal 704 quickly levels off at signal intensity level 714 which is lower than the average signal level 711 of the pre-trigger signal 701. FIG. 7C illustrates an example of a confounding event with gradual transition with full recovery. The confounding event first causes an abrupt change 702 in signal intensity, followed by a slower and longer period of transition where the signal level 721 during the transition gradually ramps up to a steady-state signal level 715. The steady-state signal level 715 of the post-transition signal 705 is similar to the average signal level 711 of the pre-transition signal 701. FIG. 7D illustrates an example of a confounding event with gradual transition with reset recovery. The confounding event first causes an abrupt change 702 in signal intensity, followed by a slower and longer period of transition where the signal level 722 gradually levels off at a steady-state signal level 716. The steady-state signal level 716 of the post-transition signal 706 is lower than the average signal level 711 of the pre-transition signal 701.

Figure 8:
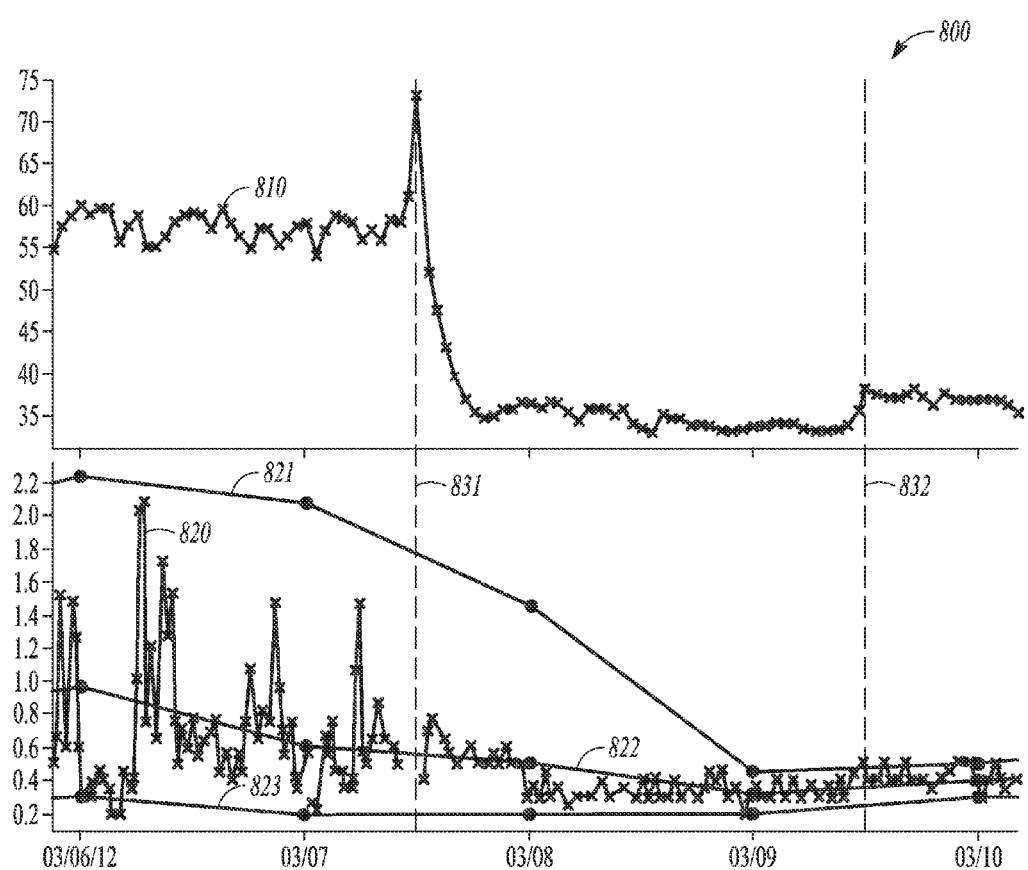
FIG. 8 illustrates an example of a confounding event's impact on CEB signals.

FIG. 8 illustrates an example of a confounding event's impact on the CEB signals sensed from various physiological sensors. In the context of detecting a target event indicative of HF decompensation, two confounding events were detected and later confirmed. As illustrated in FIG. 8, dotted line 831 marks the time of the first confounding event of a dislodgement of an RA lead from the implantable device on the patient during a procedure of mitral valve repair; and dotted line 332 marks the time of the second confounding event of repositioning of the dislodged RA lead. The two events are separated in two days.

Two sensors were used to provide CEB signals for confounding event detection. Signal 810 is a two-hour average of a transthoracic impedance signal ($Z_{RA\text{-}CAN}$) sensed from one or more electrodes on the RA lead 108A and the IMD can housing 112. Signal 820 is a 20-minute average of a tidal volume (TV) signal sensed from a respiration sensor such as using a transthoracic impedance measured from electrodes on one or more of the implantable leads 108A-C' and the can housing 112. Cyclic respiration signal can be obtained by passing the transthoracic impedance signal through a filter, and from the filtered respiration signal a breadth-by-breadth TV may be determined as the difference between the peaks and the troughs of the respiration signal. Also shown in FIG. 8 are daily characteristic values of the tidal volume: daily maximum $TV_{max}$ 821, daily median $TV_{med}$ 822, and daily minimum $TV_{min}$ 823.

The first confounding event of RA lead dislodgment causes the impedance signals $Z_{RA\text{-}CAN}$ 810 to transiently increase above the pre-transition signal baseline and then decrease to a steady level lower than the pre-transition signal intensity. The impedance changes almost instantaneously upon the occurrence of the first confounding event. With regard to the TV signal, upon the occurrence of the first confounding event, the TV intensity and the variability in TV intensity decrease. Comparing the daily characteristic values, $TV_{max}$ 821 decreases gradually from its pre-transition level within 1-2 day. In contrast, $TV_{med}$ 822 does not decrease significantly, and $TV_{min}$ 823 barely changes during course of the first confounding event.

The second confounding event of RA lead repositioning does not significantly affect the signal intensity of any TV measurement. $Z_{RA\text{-}CAN}$ increases slightly in signal intensity but instantaneously in response to the second confounding event. The consistent low TV and low $Z_{RA\text{-}CAN}$ are associated with the surgery for mitral valve repair which coincides in time with the first confounding event.

FIG. 9A illustrates an example of a method 900 for detecting and characterizing a confounding event such as using physiologically relevant data range. The method 900 is an embodiment of 602. In an example, the method 900 can be performed by the confounding event detection and analysis circuit 203 or the confounding event detection and analysis circuit 300.

At 901, a CEB physiological signal is received. In an example, the CEB physiological signal can be obtained from device-based CEB signal receiver 311, which can be coupled to ambulatory devices and associated leads, monitors, or sensors. In another example, the CEB physiological signal can be retrieved from the memory in the IMD 110 or the external system 120. Examples of CEB physiological signal can include impedance signals, respiration signals, coronary blood temperature, blood oxygen saturation, or heart sound signal. More than one physiological signal can be used to determine the physiological state.

The CEB physiological signal can be processed and one or more CEB features can be extracted at 902. The one or more CEB signal features can be statistical measurement of signal amplitude or other intensity quantities including change of signal amplitude over specified time duration, duration of the change of signal amplitude, rate of change of signal amplitude (i.e. first derivative of the signal), shift of DC level of signal amplitude, signal variability, change of signal intensity within a certain frequency range, or signal morphologies.

At 903, the one or more CEB signal features can be compared to one or more pre-determined criteria to determine the presence of a confounding event. In an example, the criterion can include pre-determined threshold values for the signal features, where the threshold values can be used to determine whether the one or more CEB signal features are physiologically relevant to the target event. If the values of the one or more CEB signal features are outside the range of physiological relevancy, then a confounding event is deemed detected; and the detected confounding event is characterized at 904. If the values of the one or more CEB signal features are within the range of physiological relevancy, then no confounding event is deemed detected.

The range of the physiological relevancy, or the thresholds for CEB signal features, can be fixed values empirically determined such as using population data or patient's historical data. For example, a change of intrathoracic impedance of greater than 50 ohms is considered physiologically irrelevant. In another example, a duration of an impedance change that sustains for less than several hours to less than two days, or a rate of change in impedance greater than 5 ohm/day or 10% of the baseline impedance value per day is considered physiologically irrelevant. In yet another example, shift in signal DC level that sustains more than three days is considered physiologically irrelevant.

The range of the physiological relevancy may also be determined using the information of the type of the confounding event, the type of physiologic sensor, the configuration of the sensor used for sensing the CEB physiological signal, or any combination thereof. In an example, a searchable data structure such as a lookup table or association map can be created and stored. The data structure can contain a plurality of values of thresholds or range of physiological relevancy. Each value can be indexed by one or more of the type of physiologic state trigger event, sensor configurations for sensing the CEB physiological signal, or the CEB signal features. Then, at 903, an appropriate threshold for physiological relevancy can be determined from the pre-stored searchable threshold structures, which can then be compared with the calculated CEB signal feature values to determine if a confounding event is detected. The detected confounding event can be characterized at 904 by extracting information regarding the time and type of the confounding event. In an example, the characteristics include the start and end time of the confounding event.

Figure 10:
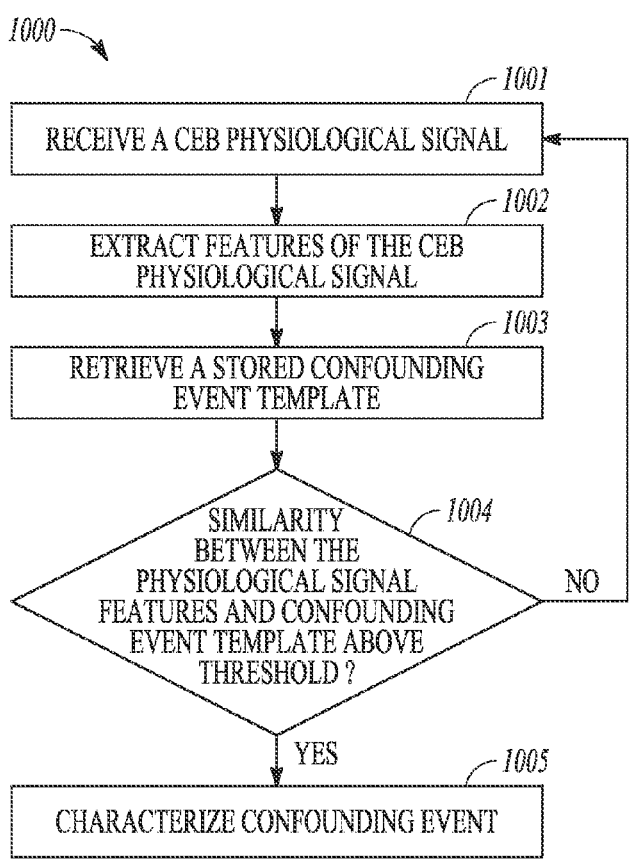
FIG. 10 illustrates an example of a method for detecting and characterizing a confounding event such as using template matching.

FIG. 10 illustrates an example of a method 1000 for detecting and characterizing a confounding event such as using template matching. The method 1000 is an embodiment of 602. In an example, the method 1000 is performed by the confounding event detection and analysis circuit 203 or the confounding event detection and analysis circuit 300.

At 1001, a CEB physiological signal is received, such as by using method 901. The features of the CEB physiological signal can then be extracted at 1002, which may be performed such as using method 902. Then, a stored confounding event template can be retrieved from memory at 1003. In an example, the confounding event template can be a morphological template computed such as using one or more segments of the CEB signal during and around the time of confounding event. The confounding event template can include at least the CEB signal morphology during the transition and recovery in response to the confounding event. The confounding event template may be obtained directly from the CEB signal, or it may be obtained from the CEB signal after signal processing such as signal filtering. For example, a low pass-filtered CEB signal, or a moving-averaged CEB signal, such as the signal levels during transition 712 in FIGS. 7C and 7D, is used to create confounding event template. The confounding event template may be created such as using one or more of patient's historical data with known confounding events, population data, or empirical knowledge of signal morphology when a confounding event is present.

In some examples, multiple confounding event templates can be used to detect a confounding event with unknown type. Each template represents a particular confounding event. In an example of detecting a confounding event using multiple templates, each template may be indexed by the type of physiologic state trigger event, sensor configurations for sensing the CEB physiological signal, or other user specified conditions.

At 1004, the received CEB signal features are compared to the confounding event template and a similarity measure is calculated. In an example, the similarity measure can be a correlation function. In another example, the similarity measure can be computed such as using the area of difference between the confounding event template and the CEB signal features with proper scaling to compensate the discrepancy of signal ranges. If the similarity is greater than a predetermined threshold, a confounding event is declared detected and the confounding event is characterized at 1005. Otherwise, no confounding event is deemed detected and the process of detecting confounding event continues.

The CEB signal can include data from sources external to devices or sensors. Examples of signals from external sources include a clinical report, a medical record, a lab test report, or a case report form. The external CEB signals can include environmental sensor signals such as temperature, humidity, or atmospheric pressure. In an example, a method is provided to directly receive the input from users the information (such as start and end time and type) of a confounding event, or automatically reads, parses and interprets textual or graphical clinical reports to detect confounding event.

Figure 11:
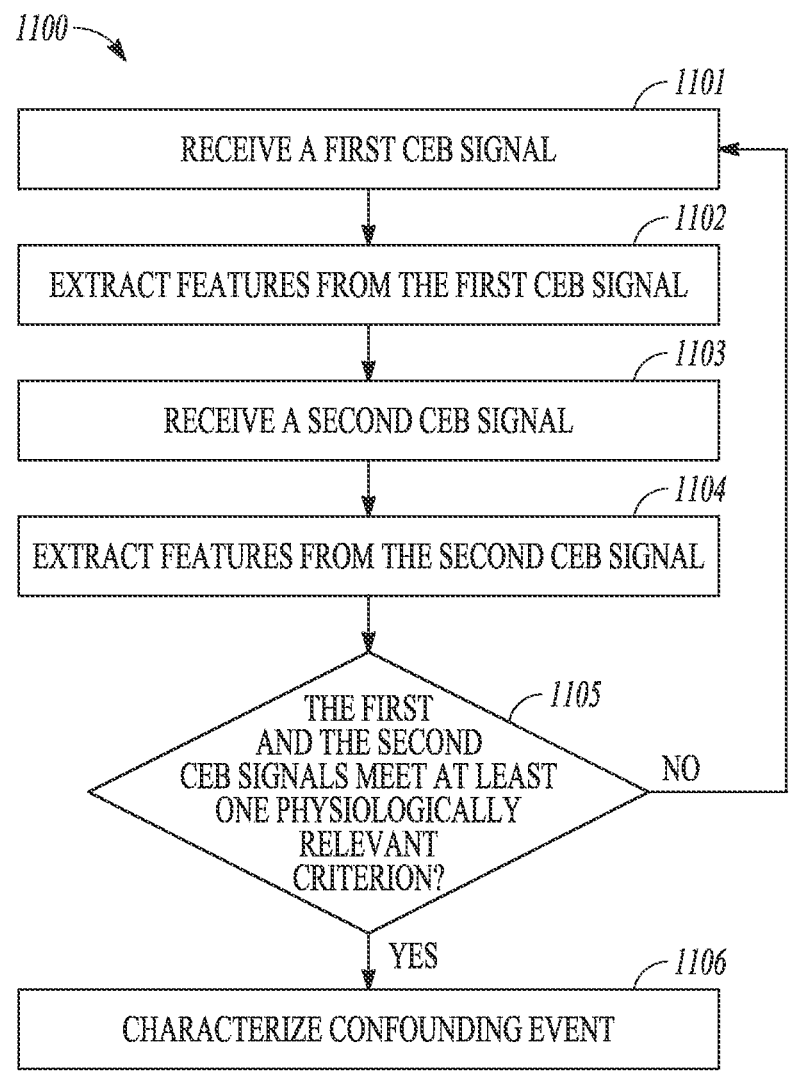
FIG. 11 illustrates an example of a method for detecting and characterizing a confounding event such as using two CEB signals.

FIG. 11 illustrates an example of a method 1100 for detecting a confounding event from more than one CEB signals or sources. The method 1100 is an embodiment of 602. In an example, the method 1100 is performed by the confounding event detection and analysis circuit 203 or the confounding event detection and analysis circuit 300.

A first CEB signal can be received at 1101 and features of the CEB signal can be extracted at 1102. The first CEB signal can be a CEB physiologic signal, CEB signals of device condition and function, or data from external sources such as a clinical report. In an example, the first CEB signal is a physiological signal, and features of the CEB physiological signal are extracted such as using method 902. In another example, the first CEB signal is a clinical report, and features of the CEB physiological signal are extracted such as using clinical report interpretation. At 1103, a second CEB signal different than the first CEB signal can be received, and features of the second CEB signal can be extracted at 1104. The second CEB signal can be a CEB physiologic signal, CEB signals of device condition and function, or data from external sources such as a clinical report. Features extracted at 1104 can be performed such as using method 902 if the second CEB signal is a physiological signal, or using clinical report interpretation if the second CEB signal is a clinical report.

At 1005, both the first and the second CEB signals can be used to determine the presence of a confounding event. In an example, a cascade detection algorithm such as a decision tree can be used at 1105. For example, the first CEB signal can be a clinical report and the second CEB signal can be a physiological signal. The clinical report (i.e., the first CEB signal) can be interpreted. If the clinical report indicates the presence of a confounding event, the extracted features from the CEB physiological signal (i.e., the second CEB signal) can be processed to confirm the presence of the confounding event using, for example, the methods of physiologic relevancy criteria at 903 or template matching at 1004.

In another example, each CEB signal can be individually processed to detect the confounding event, and a decision fusion method can be used to yield the detection decision at 1105. The decision fusion can include logic operation "OR" (where a positive detection is declared if a confounding event is detected from at least one CEB signal), "AND" (where a positive detection is declared only if a confounding event is detected from all the CEB signals), majority voting or weighted voting schemes (where, for example, a positive detection is declared if the confounding event is detected from a significant number of CEB signals), or other functions of the detection decisions or any combination thereof.

A composite CEB signal can be generated using more than one received CEB signal, or a composite feature set can be generated such as using extracted features from the more than one CEB signals. A composite CEB signal can be a linear or nonlinear function of the individual CEB signal. The composite CEB signal or the composite feature set can be compared to at least one physiologically relevant criterion, such as that in 903, to determine the presence of a confounding event. The detected confounding event can then be characterized at 1106, where the characteristics can include the start time or the end time of the confounding event.

Various variations of the FIG. 11 have also been contemplated. In an example, the second CEB signal can be provided in an on-demand mode, that is, the second CEB signal may not be received or processed until it is requested. For example, if a confounding event is declared detected from the first CEB signal, a request for confirmation can be generated. In response, a second CEB signal, such as a user confirmation input, a clinical report signal, or another CEB physiological signal, can then be received and processed to confirm the presence of the confounding event.

Figure 12:
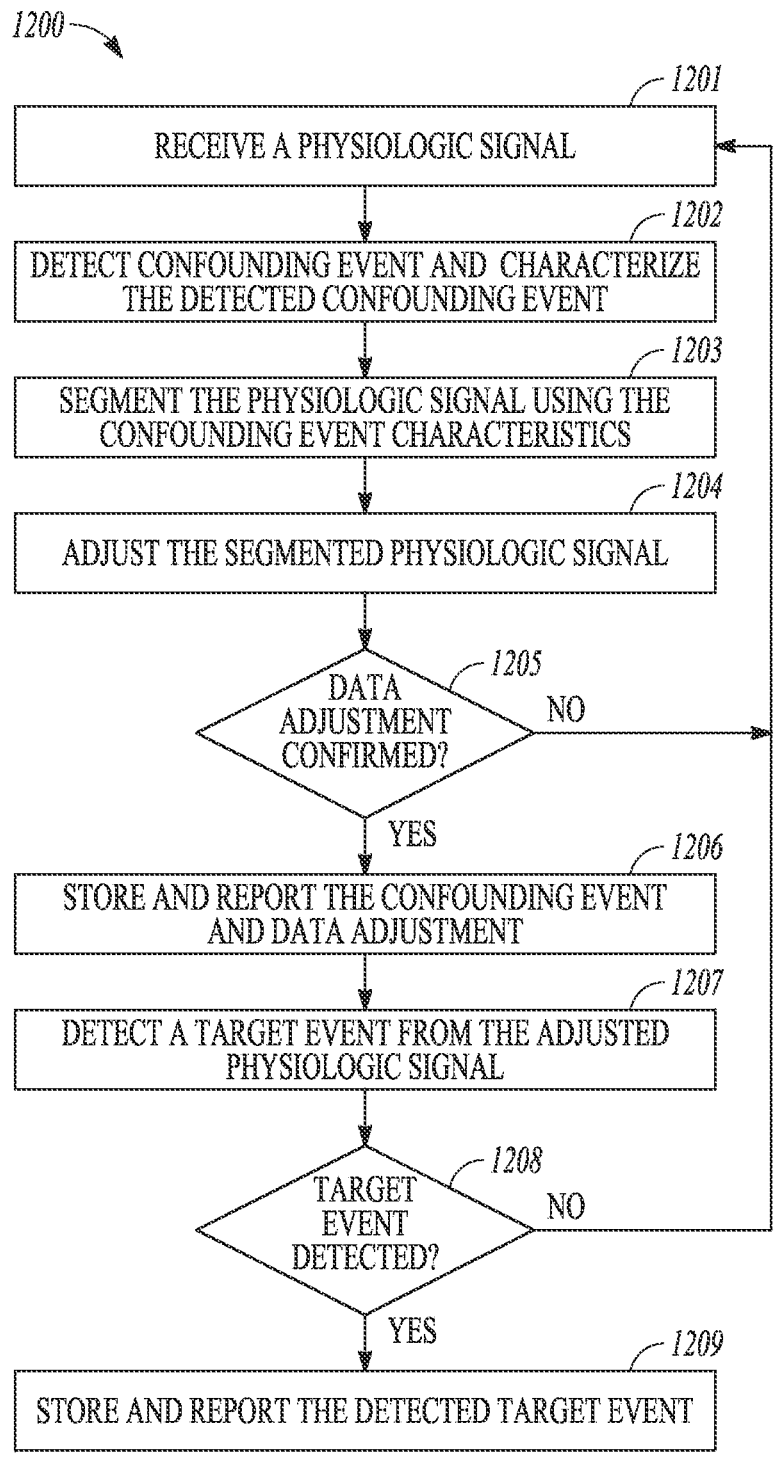
FIG. 12 illustrates an example of a method for detecting a physiologic target event in adaptation to a detected confounding event.

FIG. 12 illustrates an example of a method 1200 for detecting a target event in adaptation to the detected confounding event. The method 1200 is a specific embodiment of 600. In an example, method 1200 is performed by system 200.

At 1201, a physiological signal is received. The physiologic signal may be received from a signal sensing circuit coupled to electrodes or external sensors associated with an ambulatory medical device or a physiological monitor, or from a signal memory. At 1202, a confounding event can be detected using one or more of the physiological signal received at 1202, a different CEB physiological signal, or clinical report. The received physiological signal can be segmented into at least two segments such as using the confounding event characteristics at 1203. In an example, the start time of the confounding event ($T_0$) can be used to segment the physiologic signal into a pre-transition segment before $T_0$ and a post-transition segment after $T_0$. In another example, a transition period can be identified as between $T_0$ and $T_0+\Delta t$ where $\Delta t$ is transition duration; and the pre-transition segment is defined as the segment before $T_0$, while the post-transition segment is defined as the data after $T_0+\Delta t$ to remove the transient effect of the onset of confounding event on the physiological signal. In an example, the transition duration $\Delta t$ can be a predetermined value between 1-3 days. In another example, $\Delta t$ can be programmable and the range for $\Delta t$ can be determined using the information of the type of the confounding event or the sensing configuration of the physiological signal (i.e., electrodes used for intrathoracic impedance sensing). In another example, both the start time $T_0$ and end time $T_1$ of the confounding event can be used to segment the data. For example, the pre-transition segment may include the physiological data before $T_0$ and the post-transition segment may include the physiological data after T1. In another example, the post-transition segment can include the physiological data after $T_1+\Delta t$ where $\Delta t$ is transition duration.

At 1204, the segmented physiologic signal can be adjusted to remove or reduce the impact of the confounding event on the physiological signal. The adjustment can be made to one or both of the pre-transition segment and the post-transition segment. When both segments are adjusted, the adjustment of one segment can be made such as by using signal characteristics of the other segment. Alternatively, the adjustment of one segment can be made without using the signal characteristics of other segment of the signal. The adjustment process of one segment can be independent of the adjustment of the other segment. In some examples, more than two segments can be made and each segment can be adjusted.

In an example, the segment to adjust can be determined by the type of the detected confounding event. For example, if the confounding event is a "steady" event that has sustained effects on the physiological signal such that the signal is unlikely to recover over time (for example, the signal as illustrated in FIG. 7B), then only the pre-transition segment is adjusted. Post-transition segment is not to be adjusted because it represents the new and steady patient condition. Example of the steady event can include a change of device programming. If the confounding event is an "acute" event that has a transient effect on the physiological signal such that the signal is expected to recover towards the pre-transition value over time (as illustrated in FIG. 7C), then the post-transition segment can be adjusted because it reflects a temporary patient condition that would resolve over time. Examples of acute event can include a surgical intervention, a replacement of the device either at the same location or at a different location, or a pocket revision. If the confounding event is an acute event that causes the signal following the event to recover towards a value different than the pre-transition value (as illustrated in FIG. 7D), then both the pre- and post-transition segment can be adjusted because the baseline is changing.

The adjustment of the pre-transition or post-transition segment can be made by comparing a first metric determined from the pre-transition segment to a second metric determined from the post-transition segment, determining an adjustment factor from the comparison, and adjusting the selected segment(s) using the adjustment factor. In an example, the second metric can be a "recent" signal level computed as a central tendency measure over a short period in the post-transition segment, and the first metric can be a "baseline" signal level computed as the central tendency measure over relatively longer time window into the past. Examples of central tendency measure can include mean, median, weighted-mean, or mode. In another example, the first metric can be a central tendency measure over a short period $\Delta_0$ ending at the beginning of the confounding event ($T_0$), that is, ($T_0-\Delta_0$, $T_0$); and the second metric can be a central tendency measure over a short period $\Delta_1$ beginning at the end of the confounding event ($T_1$), that is, ($T_1$, $T_1+\Delta_1$).

Various embodiments of adjustment factor, determined from the first and the second metrics, have been contemplated. In an example, the adjustment factor can be a difference between the second metric and the first metric. The adjustment factor can then be added to the pre-transition segment of physiological data. In another example, the adjustment factor can be a ratio between the second metric and the first metric. The pre-transition segment of physiological data can then be scaled by multiplying the adjustment factor. In another example, the adjustment factor can be time-varying, that is, the amount of adjustment can be dependent on the timing location of the data with reference to the start time or end time of the confounding event. For example, to adjust the pre-transition segment, the value of the adjustment factor can increase with time up to the transition start-time ($T_0$). In another example, to adjust the post-transition data segment, the value of the adjustment factor can decrease with time from the transition end-time ($T_1$). In another example, a base value of an offset ($D_0$) can be computed as the difference between the second metric and the first metric. The time-varying adjustment factor $D_t$ can be an exponential function of time in reference to $T_0$ or $T_1$:

$$\begin{cases} D_t = D_0 \cdot e^{t-T_0} & \text{if } t \leq T_0 \\ D_t = D_0 & \text{if } T_0 < t < T_1 \\ D_t = D_0 \cdot e^{T_1-t} & \text{if } t \geq T_1 \end{cases}$$

The adjustment of the signal segment can be made on derivatives of the physiological signal. For example, a confounding event may cause abrupt change in signal intensity. Such change in signal intensity may be detected as a peak or a trough in first derivative of the physiological signal (i.e., point-to-point difference). To remove the abrupt change, the derivative signal may be smoothened, for example, by replacing the identified peak or trough derivatives with the mean derivatives calculated over a pre-transition period, so that the signature of the confounding event on the physiological signal can be eliminated or lessened. The smoothened derivative signal may then be reconstructed by taking the integral from the first point of the pre-transition period.

At 1204 a mode of adjustment can be determined. The mode of adjustment, including a transient adjustment or a permanent adjustment, can determine the amount of data to be adjusted in the selected segment. In an example, the mode of adjustment can be determined such as using one or more of a type of the detected confounding event, a type of the physiologic signal, or a sensing configuration of the physiological signal. For example, if the pre-transition segment is chosen to be adjusted, then the adjustment can be performed on the data within a data window ($T_0-t_H$, $T_0$) from the pre-transition segment, where $T_0$ is the start time of the confounding event, and the programmable parameter $t_H$ controls how far back in the signal history from $T_0$ the data in the pre-transition segment should be adjusted. As an example, $t_H$ can take a value between 1 to 8 weeks. In another example, $t_H$ can be the same as the window size used for updating a signal baseline. For example, if the signal baseline is calculated as the moving average of data over 2 months, then $t_H$ can also be set to 2 months. In an example, a patient's entire historic data can be adjusted.

If the post-transition segment is chosen to be adjusted, then the adjustment can be made within a data window after $T_0$. In an example, the post-transition data window for adjustment can be chosen to be $(T_0, T_0+t_C)$. In another example, the post-transition data window for adjustment can be $(T_1, T_1+t_C)$. The programmable parameter $t_C$ controls how much "forward" from the start $(T_0)$ or the end $(T_1)$ of the confounding event the data in the post-transition segment are to be adjusted. To ensure that the complete signal transition can be observed and adjusted, $t_C$ can be programmed to a value greater than the expected duration of transition. For example, $t_C$ can be programmed to two days or longer.

In an example, $t_C$ can be a predetermined fixed value. The adjustment can be made only when all data within the data window become available. Then, the signal adjustment is a one-time operation on the data within the data window. In another example, $t_C$ is not fixed value; and the post-transition segment can be adjusted while current signal data are being collected. This repeated and continuous post-transition segment adjustment can provide continuous presentation of the adjusted data for patient monitoring and timely detection of health state change and notification to the caregiver. In an example, the post-transition segment adjustment method can be updated while the data from the post-transition segment are collected and assessed. For example, the adjustment factor, such as the scaling factor applied to the post-transition segment, may be tuned dynamically while new post-transition data become available. Each adjustment attempt can use the unadjusted data and produce a new set of adjusted post-transition values. The adjustment of the post-transition segment can continue for as long as the adjusted data are used to detect a health state change.

In an example, both the pre-transition and the post-transition segments can be adjusted. Methods discussed above pertaining to pre-transition segment adjustment or to post-transition segment adjustment can be applied to the concurrent pre-transition and post-transition segment adjustment. For example, a first adjustment factor (e.g., a DC shift or a scaling factor) can be applied to the pre-transition segment and a second adjustment factor can be applied to the second-transition segment, and the pre-transition segment adjustment and the post-transition adjustment can be performed sequentially or concurrently.

At 1205, a notification of detection of confounding event and the data adjustment can be generated and prompted for user confirmation. The notification can include an indication that the pre-transition or post-transition segment are to be adjusted, the segment(s) selected for adjustment, or the mode of adjustment (i.e., permanent or transient adjustment). In an example, the notification and the request for confirmation (RFC) may be generated and presented in a sequence of steps. For example, a first notification and RFC can be presented to the user upon the detection and characterization of a confounding event. Once a confirmation is received, a second notification and RFC can be presented upon the data segmentation and adjustment. The confirmed confounding events and the adjusted physiological signal can be stored in a memory at 1206.

The adjusted physiological signal can be at 1207 to detect a target event. In an example, the target event is an event indicative of HF decompensation status. A HF decompensation detection algorithm can compute an HF decompensation index such as using the adjusted physiologic data and determine whether an event indicative of HF decompensation is detected such as by comparing the decompensation index to a pre-determined threshold value.

The decompensation index can be a quantitative measure indicating the presence or severity of a physiologic condition precipitating an HF decompensation episode, such as excessive intrathoracic fluid accumulation. In another example, the decompensation index can be an accumulated deviation of the sensed physiological signal from a reference signal over time. The reference signal can represent the trend of the physiological signal intensity, such as signal amplitude or a function of the signal amplitude, or the signal's power spectral density or a function of the power spectral density. In an example, the reference signal can be a moving average of the physiological data over a specified time period. In another example, the reference signal can be a low-pass or band-pass filtered physiological data with pre-determined filter coefficients.

The deviation can be computed as a difference between the intensity of the sensed physiological signal and the reference signal. In an example, the intensity of the sensed physiological signal can include a central tendency measure of the signal amplitude over a specified time such as 3-10 days. In another example, the decompensation index can be accumulated only if a certain criterion is met, such as the difference between the signal intensity and the decompensation index being greater than a specified threshold. Other examples of decompensation index can include the cumulative sum in detecting persistent shifts in the trended signal found in Brockway et al., U.S. Pat. No. 7,761,158, entitled "Detection of Heart Failure Decompensation Based on Cumulative Changes in Sensor Signals," filed Dec. 20, 2005, which is incorporated herein by reference in its entirety.

At 1208, a decision can be made as to whether a target event is detected. For example, in the context of detecting HF decompensation, the computed decompensation index can be compared to a specified threshold at 1208. If the decompensation index is greater than the threshold, then a target event is detected. At 1209, a report is generated to inform the user the detected target event. Examples of the report can include a textual or graphical message, a sound, an image, or any combination thereof. If the decompensation index is greater than the threshold, then no target event is detected, and the detection continues with receiving the physiological signal at 1201.

Figure 13A:
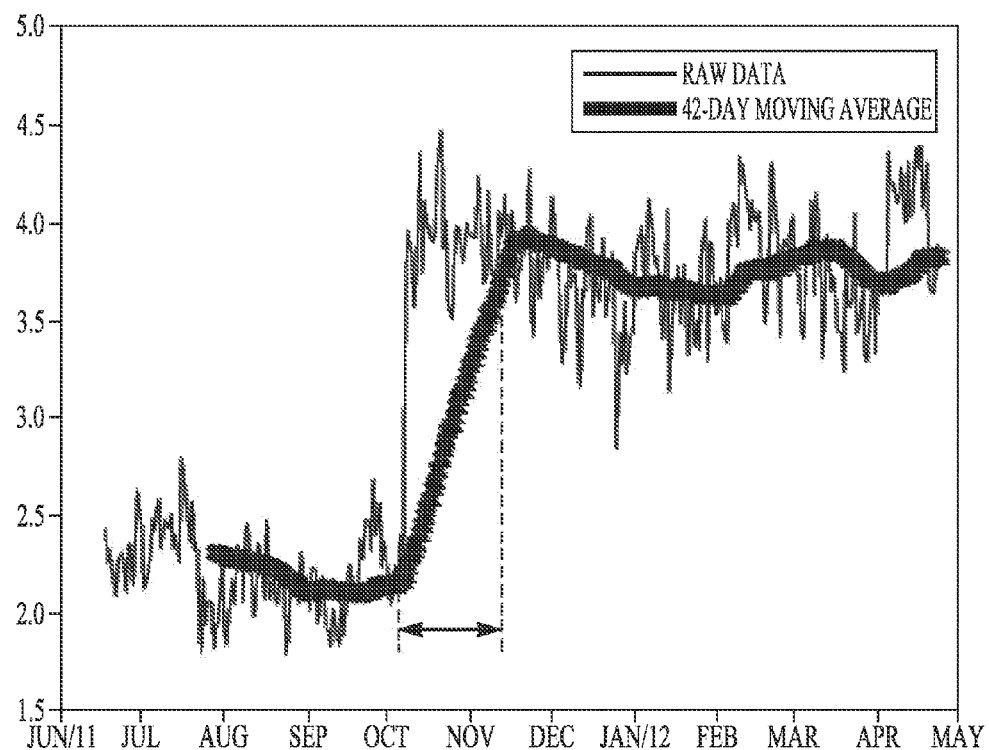
FIGS. 13A-B illustrate examples of pre-transition signal adjustment using the information of the detected confounding event.
Figure 13B:
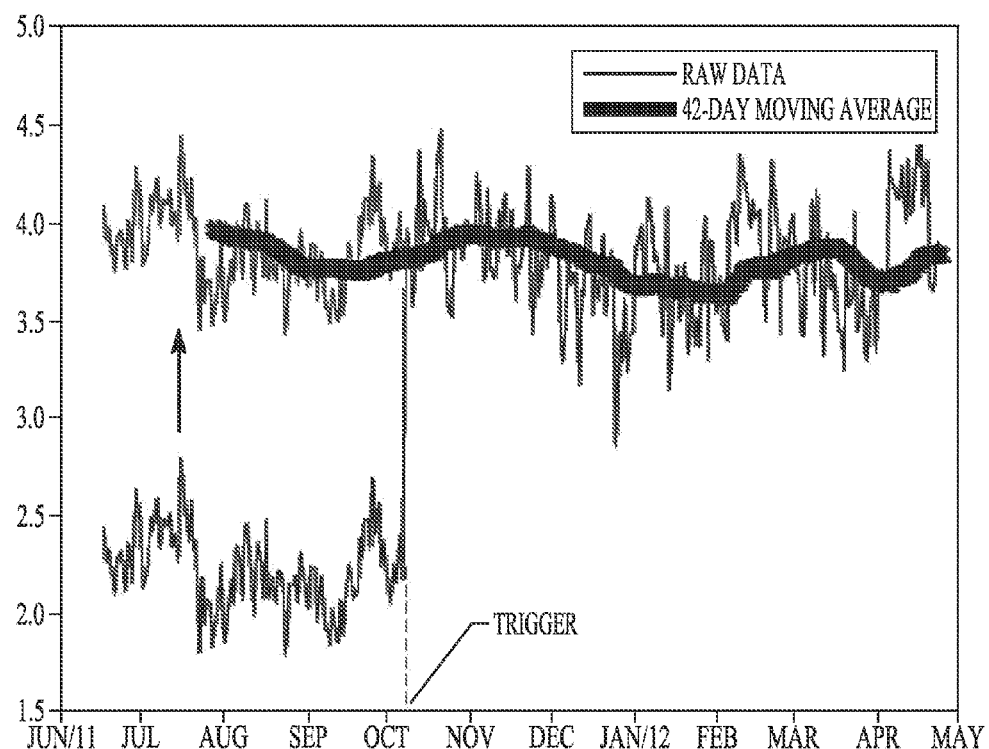

FIGS. 13A-B illustrate examples of pre-transition signal adjustment using the information of the detected confounding event such as using the adjustment method at 1204, as discussed above. The physiological signal illustrated in FIG. 13A is the amplitude signal of first heart sound (S1) computed from a heart sound (HS) signal. In this example, the HS signal was collected in a span of 12 months from an accelerometer coupled to an IMD 110. The y-axis indicates the intensity of the S1 amplitude in the unit of milli-G. In an example, the HS sensor can be a microphone sensor; and the HS sensor may be located within IMD 110, on a lead, or externally in a patch. S1 amplitude can be measured as the peak or peak-to-peak deflection on the HS signal or a root-mean-square of a segment of the HS signal around the peak of S1. Also shown in FIG. 13A is the average baseline S1 amplitude signal 1322. A confounding event, later confirmed to be a device reprogramming of atrial-ventricular pace delay, occurred in around October 2011. The confounding event causes an abrupt increase 1312 in S1 amplitude signal occurred within one day. The post-transition signal 1313 remains at a level with a higher DC offset than the pre-transition signal 1311. The "baseline" of the S1 amplitude is computed as the moving-average of the S1 amplitude collected in consecutive 42 days. Due to the abrupt change in S1 amplitude 1312, the moving-average S1 amplitude, which is a low-pass filtered signal of the raw S1 amplitude signal, demonstrates a slow ramp-up 1322 from the pre-transition baseline 1321. No baseline data was obtained during the transition; and a stable post-transition baseline 1323 was not achieved until 42 days after the onset of the confounding event.

FIG. 13B illustrates the same S1 amplitude signal as in FIG. 13A which is subsequently adjusted such as using the information of the start time of the confounding event and the post-transition and the pre-transition segments signal characteristics. In this example, a pre-transition baseline signal (i.e., 42-day moving average) 1321 is compared to the post-transition baseline signal 1313. An adjustment factor, computed as the difference between the post-transition baseline value and the pre-transition baseline value, is added to the pre-transition signal 1311. The resulting adjusted pre-transition signal 1331 has the same signal morphology as the unadjusted pre-transition signal 1311, but different DC offset. As a result, the adjusted pre-transition baseline signal 1341 has a comparable DC offset level as the post-transition baseline signal 1342, and the impact of the confounding event on the S1 amplitude signal (i.e., the abrupt signal change 1312) is substantially reduced.

Figure 14A:
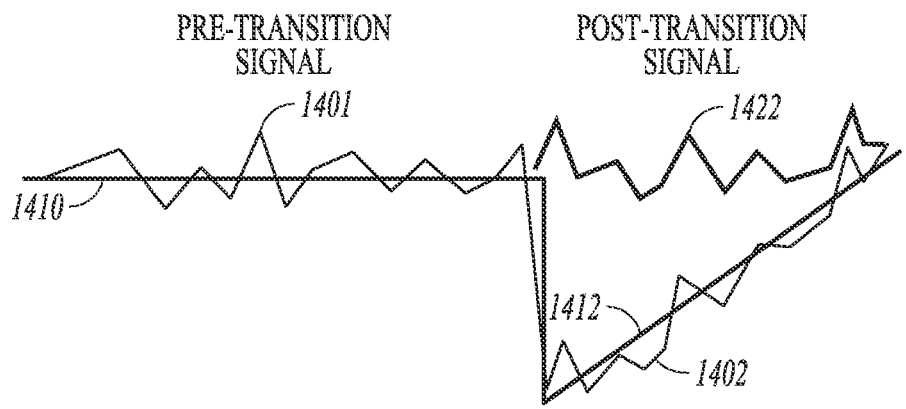
FIGS. 14A-B illustrate examples of post-transition signal adjustment using the information of the detected confounding event.
Figure 14B:
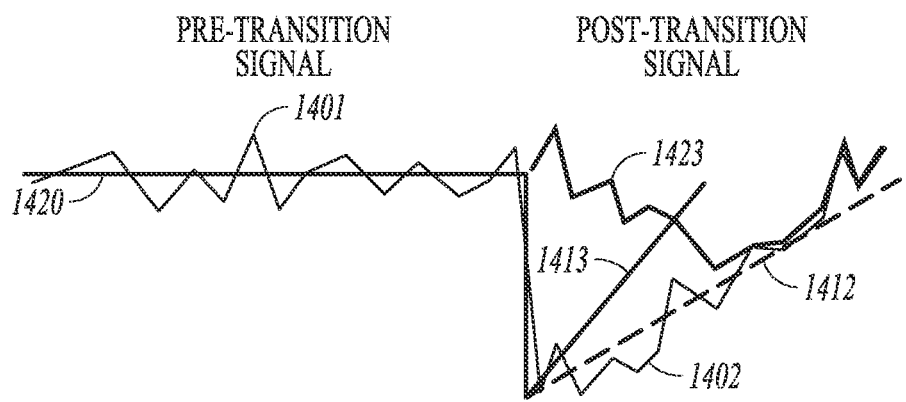

FIGS. 14A-B illustrate examples of post-transition signal adjustment using the information of the detected confounding event. In this example, a template is used in data adjustment. The template can be created for a particular confounding event using a particular type of physiological signal. The template can represent the expected behavior of the signal (e.g., statistical property like the mean or DC trend, or morphological characteristics) in response to a given confounding event.

As illustrated in FIG. 14A, a confounding event can cause an abrupt and transient reduction in the intensity of a physiological signal 1401. Abrupt decrease in intrathoracic impedance may be a result of, for example, an open chest surgery that transiently reduces the patient's tidal volume. Following the abrupt change, the intensity of the post-transition signal 1402 gradually recovers. The confounding event can be detected and characterized such as using one of the methods 900, 1000, or 1100. According to the type of the confounding event and the type of physiological signal used for target event detection, an appropriate template can be retrieved from the memory. In the example as illustrated in FIG. 14A, the template may represent the expected pattern of changes in physiological signal intensity. The template can include a pre-transition branch 1410 with a fixed amplitude extended for a specified duration, and a post-transition branch 1412 with a linear ramp with a pre-determined slope. The template can be matched to the impedance signal before and after the transition event. In an example, the match can be performed by aligning a fiducial point on the template, such as the point of change in the signal intensity, to the start time of the confounding event ($T_0$) on the physiological signal. In another example, prior to template matching, the template can be scaled so that the amplitude of the pre-transition branch 1410 is equivalent to the average intensity of the physiological signal 1401. Then, by subtracting the template from the unadjusted impedance signal, the ramp-up trend is removed from the unadjusted post-transition signal 1402. The resulting adjusted post-transition segment 1422 has about the same DC offset level as the pre-transition signal 1401.

The template can include a first-order response curve with a given step response and a time constant for post-transition signal recovery. Examples of the recovery curve can include exponential, power, logarithm functions, or other non-parametric numeric descriptors of the curve. In an example, the slope of post-transition branch of the template 1412, or similarly the step response curve and time constant, can be variable within an acceptable range for a given type of confounding event. For example, the time constant of the post-transition recovery curve for the confounding event of post chest surgery can vary between 1 and 2 months. The template, including the time constant of recovery curve, can be adjusted automatically as the new data is gathered.

FIG. 14B illustrates a mismatch between a template and a physiological signal. The selected template includes a pre-transition branch 1420 and a post-transition branch 1413. The post-transition branch 1413 does not match the post-transition physiological signal 1402. Specifically, the post-transition physiological signal 1402 has a slower signal recovery rate than the post-transition branch of the template 1413. Consequently, the adjusted post-transition physiological signal 1423 demonstrates a decline in signal intensity because of the steeper slope of the post-transition branch of the template 1413. The mismatch between the template and the physiological signal during a confounding event can trigger an alert to the user. The alert may include the information of mismatch, unexpected rate of post-transition recovery in the physiological signal, or possible complications associates with the confounding event. The alert may also be generated during the data adjustment confirmation at 1205.

In an example, in response to a detected mismatch between the template and the physiological signal during a confounding event, a different template can be used to re-adjust the post-transition signal 1402. In another example, the mismatched template can be modified by adjusting the post-transition branch of the template 1413, and the adjusted template can be reapplied to the physiological signal.

Figure 15:
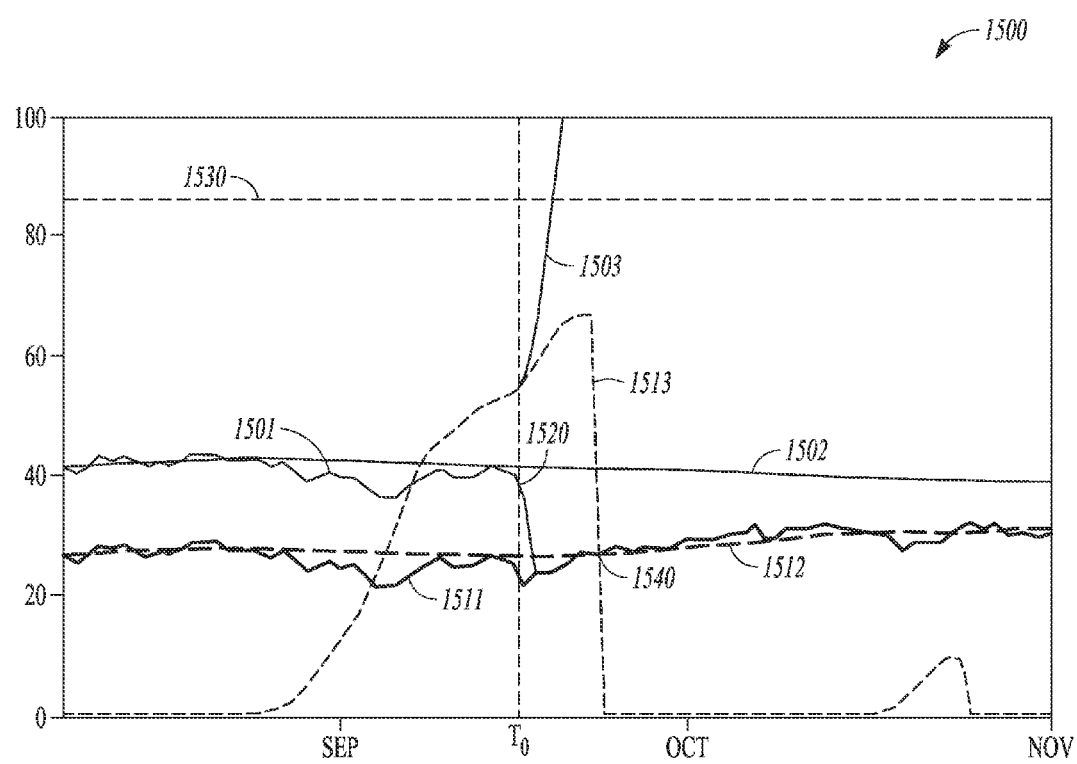
FIG. 15 illustrates an example of a method for detecting an HF decompensation event.

FIG. 15 illustrates an example of a method 1500 for detecting an HF decompensation event. In this example, an HF decompensation event is detected from a physiological signal 1501 using an HF decompensation algorithm such as the method 1200. A reference signal 1502 can be computed such as using the physiological signal 1501. In an example, the reference signal 1502 can be a low-pass filtered or moving-averaged physiological signal 1501. A HF decompensation risk index (DI) signal 1503 can be computed and updated such as using the comparison between the intensity of the present physiological signal 1520 and the reference signal 1502. The DI signal 1503 can be obtained such as using the method 1207. The DI can be accumulated if the present physiological signal 1520 is smaller than the reference signal 1502 beyond a range of tolerance, and the DI can be reset to a pre-determined value if the present physiological signal 1520 is greater than the reference signal 1502 beyond a range of tolerance, that is, $$DI(t) = \begin{cases} DI(t-1) + f(x(t), Ref(t)), & \text{if } x(t) - Ref(t) \leq \delta \\ DI(0), & \text{if } x(t) - Ref(t) > \delta \end{cases}$$

where x(t) is the intensity of the physiological signal at time t, Ref(t) the reference signal intensity at time t, DI(t) the DI at time t, DI(0) the pre-determined value of DI, δ the predetermined tolerance for comparing x(t) and Ref(t), and f(x(t), Ref(t)) the accumulation factor as a function of x(t) and Ref(t). In an example, f(x(t), Ref(t)) is proportional to the difference between Ref(t) and x(t), that is, f(x(t), Ref(t))=k*(Ref(t)−x(t)), where k is a positive scalar.

As illustrated in FIG. 15, a confounding event occurring at time ($T_0$) causes an abrupt decrease 1520 in the physiological signal 1501. The reference signal 1502 decreases slightly but is less impacted by the confounding event than the physiological signal 1501. The reference signal 1502 remains greater than the physiological signal 1520 before, during, and after the confounding event. As a result, the DI accumulates and monotonically increases. When the DI increases above a pre-set threshold 1530, a HF decompensation event is detected, and an alert can be issued. The detection, however, is a false alarm detection because it is triggered by the confounding event that causes the abrupt change 1520 in the physiological signal 1501. The DI signal remains above the threshold for over a month and remains insensitive to most physiological changes in signal 1520.

The false alarm may be avoided using the disclosed method, such as that illustrated in 1200. Upon the detection of the confounding event from the signal 1501, the confounding event can be characterized and the start time ($T_0$) of the confounding event is identified. The physiological signal 1501 can be segmented into the pre-transition and post-transition segments, and the pre-transition segment can be adjusted using the information of the confounding event detected from the signal 1501. In an example, a method as illustrated in FIG. 13 can be used for pre-transition segment adjustment. The signature of the confounding event can be removed or greatly lessened from the adjusted signal 1511, as illustrated in FIG. 15. The reference signal 1502 can be updated accordingly such as using the adjusted physiological signal 1511 to obtain an adjusted reference signal 1512. The "adjusted" DI signal 1513 can then be computed using the adjusted physiological signal 1511 and the adjusted reference signal 1512. As illustrated in FIG. 15, the adjusted DI can be accumulated until the accumulation condition fails at 1540 when the adjusted physiological signal intensity is greater than the adjusted reference signal over a tolerance δ, and the adjusted DI is reset to the initial value. Because DI does not exceed the DI threshold 1530, no HF decompensation event is detected. The adjusted DI remains sensitive to deviations of the physiological signal from its reference.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An ambulatory medical device, comprising:
   a signal receiver circuit, configured to receive a physiologic signal, for detecting a physiologic target event or condition of a patient;
   a confounding event detection and analysis circuit, including a confounding event-bearing (CEB) signal receiver circuit configured to receive at least one CEB signal, and a confounding event detector configured to detect the presence of a confounding event from the at least one CEB signal, different from the physiologic target event or condition;

a signal processing circuit, configured to
segment the physiologic signal into at least first and second segments based on a detected start time of the confounding event, the first segment exhibiting a different steady-state signal level than the second segment, and
adjust at least one of the first or second segments;
wherein adjusting at least one of the first or second segments of a physiologic signal includes computing and using the difference between the at least one of the first or second segments and a reference signal over a specified time period relative to a start time of the confounding event;

a target event or condition detector circuit, configured to detect the physiologic target event or condition from the at least one of the first or second adjusted segments of the physiologic signal;

wherein the confounding event detection and analysis circuit is further configured to
determine the presence of the confounding event according to whether or not the at least one CEB signal meets at least one physiologically relevant criterion comprising a range of values having physiological relevance to the target event, and
indicate the presence of a confounding event if the CEB signal falls outside of the range of values having physiological relevance to the target event.

2. The device of claim 1, wherein the signal receiver circuit is configured to be coupled to at least one of a signal memory or a signal sensing circuit, and wherein the signal sensing circuit is configured to sense the physiologic signal.

3. The device of claim 1, wherein the confounding event detector is configured to detect, from the at least one CEB signal, an event indicative of at least one of a change of integrity of the device, a change of configuration of the device, a change of interaction between the device and the patient, a change of patient environment, a change of the patient condition, a replacement of the device, and a medical event.

4. The device of claim 1, the confounding event detection and analysis circuit further including a confounding event characterizer configured to compute characteristic parameters of the detected confounding event;
wherein segmenting the physiologic signal into at least the first and second segments by the signal processing circuit further includes using at least one characteristic parameter of the detected confounding event, the characteristic parameter selected from the group consisting of a stop time, a duration, and a type of the detected confounding event; and
adjusting the at least one of the first and second segments by the signal processing circuit further includes using a comparison between a first metric determined from the first segment and a second metric determined from the second segment.

5. The device of claim 1, wherein the signal processing circuit is configured to determine a mode of adjustment using at least one of a type of the detected confounding event, and a type of the physiologic signal, and wherein the mode of adjustment is selected from a transient adjustment and a permanent adjustment.

6. The ambulatory medical device of claim 1, wherein the confounding event detection and analysis circuit is further configured to include the range of values having physiological relevance to the target that are determined using population data or the patient's historical data.

7. The ambulatory medical device of claim 1, wherein the physiologic signal received by the signal receiver circuit includes intrathoracic impedance; and
wherein the at least one physiologically relevant criterion comprises a change of intrathoracic impedance of less than 50 ohms.

8. The ambulatory medical device of claim 1, wherein the physiologic signal received by the signal receiver circuit includes intrathoracic impedance; and
wherein the at least one physiologically relevant criterion comprises a rate of change in impedance less than 5 ohm/day or 10% of a baseline impedance value per day.

9. The ambulatory medical device of claim 1, wherein the reference signal is a moving average of the physiological data over a specified time period.

* * * * *